(12) United States Patent
John et al.

(10) Patent No.: US 7,309,680 B2
(45) Date of Patent: Dec. 18, 2007

(54) MOLYBDENUM-SULFUR ADDITIVES

(75) Inventors: Joby V. John, Prospect Park, NJ (US); Ronald P. Wangner, Garden City, NY (US); Antonio Gutierrez, Mercerville, NJ (US); Gregory C. Giffin, Martinsville, NJ (US)

(73) Assignee: Infineum International Limited (GB)

( * ) Notice: Subject to any disclaimer, the term of this patent is extended or adjusted under 35 U.S.C. 154(b) by 609 days.

(21) Appl. No.: 10/611,228

(22) Filed: Jul. 1, 2003

(65) Prior Publication Data

US 2004/0132627 A1 Jul. 8, 2004

(30) Foreign Application Priority Data

Jul. 8, 2002 (EP) ................... 02078011

(51) Int. Cl.
*C10M 139/00* (2006.01)
*C07F 11/00* (2006.01)

(52) U.S. Cl. ............... 508/363; 508/364; 508/365; 508/379; 556/38; 556/57; 556/61

(58) Field of Classification Search ............. 508/363, 508/364, 365, 379
See application file for complete search history.

(56) References Cited

U.S. PATENT DOCUMENTS

| | | | | |
|---|---|---|---|---|
| 3,400,140 | A | 9/1968 | Rowan et al. | 260/429 |
| 3,509,051 | A | 4/1970 | Homer et al. | 252/33.6 |
| 4,097,369 | A | 6/1978 | Ebel et al. | 208/180 |
| 4,289,635 | A | 9/1981 | Schroeck | 252/32.7 E |
| 5,631,213 | A * | 5/1997 | Tanaka et al. | 508/363 |
| 5,916,851 | A * | 6/1999 | Hosonuma et al. | 508/363 |
| 6,043,200 | A * | 3/2000 | Carroll et al. | 508/332 |
| 6,072,065 | A | 6/2000 | Chavet | 554/195 |
| 6,110,878 | A * | 8/2000 | McConnachie et al. | 508/363 |
| 6,232,276 | B1 * | 5/2001 | Stiefel et al. | 508/363 |
| 6,358,894 | B1 * | 3/2002 | Leta et al. | 508/363 |
| 6,528,463 | B1 * | 3/2003 | Gatto et al. | 508/367 |
| 6,541,429 | B2 * | 4/2003 | McConnachie et al. | 508/363 |
| 6,569,820 | B2 * | 5/2003 | McConnachie et al. | 508/363 |
| 6,852,679 | B2 * | 2/2005 | Hartley et al. | 508/365 |
| 6,953,771 | B2 * | 10/2005 | McConnachie et al. | 508/363 |

FOREIGN PATENT DOCUMENTS

| | | |
|---|---|---|
| WO | WO85/04896 | 11/1985 |
| WO | WO98/26030 | 6/1998 |
| WO | WO99/31113 | 6/1999 |

* cited by examiner

*Primary Examiner*—Ellen M. McAvoy

(57) ABSTRACT

A process for making an additive comprising one or more oil-soluble or oil-dispersible molybdenum-sulfur compounds, said process comprising the steps of:

(I) reacting in a polar medium a reactant molybdenum compound (A) and a source of a ligand (B), which ligand (B) is capable of rendering the or each molybdenum-sulfur compound oil-soluble or oil-dispersible; and (II) reacting a compound (C), which is capable of reacting with labile sulfur, either with (a) the reaction mixture of step (I) after the reaction of (A) and (B) has begun or (b) the product of step (I).

The additive has improved color characteristics and a lubricating oil composition comprising said additive is more benign to corrosion of metals.

11 Claims, No Drawings

MOLYBDENUM-SULFUR ADDITIVES

The present invention relates to an additive comprising one or more molybdenum-sulfur compounds, and an additive composition and an oil composition, preferably a lubricating oil composition, comprising said additive. The invention also concerns a process for making an additive comprising one or more molybdenum-sulfur compounds. The additive, additive composition and oil composition of the invention have improved properties, such as improved colour. Further, the oil composition of the invention demonstrates acceptable copper corrosion, and satisfactory oxidation control and friction-reducing characteristics.

Lubricant additives are sought which provide performance properties, such as fuel economy and oxidation control. However, the lubricant additives also have to meet certain other requirements, such as to demonstrate acceptable corrosion of metals used in the engine and acceptable degradation of seals used in the engine, and have a minimum amount of, preferably no, chlorine because of the environmental and waste disposal concerns. Further, the visual appearance (for example, colour) of a lubricant additive is also an important characteristic because lubricant additives that are dark in colour result in a darker lubricating oil composition: dark lubricating oil compositions are not desired by manufacturers of lubricating oil compositions and users of lubricating oil compositions.

Certain oil-soluble molybdenum-sulfur compounds are known as lubricant additives, such as dinuclear molybdenum compounds characterised by the oxidation state of Mo(V) and trinuclear molybdenum compounds characterised by the oxidation state of Mo(IV).

Trinuclear molybdenum-sulfur additives are described in WO98/26030, WO99/31113, WO99/66013, EP-A-1 138 686 and EP-A-1 138 752. However, those additives either contain a high amount of chlorine or have a high ratio of sulfur to molybdenum due mainly to the presence of sulfur species, including elemental sulfur, which are sometimes referred to as labile, free or active sulfur. Additives containing those sulfur species have been found to be corrosive to metals, such as copper and copper alloys which are widely used as bearings and bearing liners. They have also been found to cause the degradation of elastomeric materials, which are used as seals.

It would be desirable to be able to use higher levels of molybdenum-sulfur additives, particularly trinuclear molybdenum-sulfur additives, in order to benefit from their performance properties, but the problems associated with copper corrosion and/or seal degradation, and chlorine content preclude this. A solution is to use co-additives, such as derivatives of triazole and thiadiazole, that protect against such corrosion or degradation, but the use of such co-additives is expensive and a source of further complications in lubricating oil compositions.

An alternative solution is to use molybdenum-sulfur additives that do not contain labile sulfur. A method of obtaining such additives involves heating the additives to a high temperature. However, this method results in darker molybdenum-sulfur additives.

It has now been found that a certain process provides an improved molybdenum-sulfur additive, said additive having a satisfactory colour appearance, a low chlorine content, and an acceptable sulfur to molybdenum ratio so that a lubricating oil composition containing said additive is significantly more benign to copper corrosion and seal degradation.

Accordingly, in a first aspect, the present invention provides a process for making an additive, preferably having a sulfur to molybdenum ratio, based on mass, of 1.45 to 2.25, comprising one or more oil-soluble or oil-dispersible molybdenum-sulfur compounds, said process comprising the steps of:
(I) reacting in a polar medium a reactant molybdenum compound (A) and a source of a ligand (B), which ligand (B) is capable of rendering the or each molybdenum-sulfur compound oil-soluble or oil-dispersible; and
(II) reacting a compound (C), which is capable of reacting with labile sulfur, either with (a) the reaction mixture of step (I) after the reaction of (A) and (B) has begun or (b) the product of step (I).

In second aspect, the present invention provides an additive obtainable, preferably obtained, by the process according to the first aspect.

In a third aspect, the present invention provides an additive comprising one or more oil-soluble or oil-dispersible molybdenum-sulfur compounds, wherein the additive has:
(i) a colour reading of at most 5.5, when measured according to ASTM D1500 on a sample containing white oil and the additive in an amount of 110 ppm by mass of elemental molybdenum, based on the mass of the sample;
(ii) a chlorine content of less than 900 ppm by mass, based on the mass of the additive, according to ASTM D6443; and
(iii) a sulfur to molybdenum ratio, based on mass, in the range of 1.45 to 2.25, the amount of sulfur and molybdenum being measured according to ASTM D5185.

In a fourth aspect, the present invention provides an additive composition comprising a diluent fluid, an additive according to either the second or third aspect, and one or more co-additives.

In a fifth aspect, the present invention provides a an oil composition, preferably a lubricating oil composition, comprising a major amount of an oil of lubricating viscosity, and added thereto or admixed therewith, a minor amount of an additive composition according to the fourth aspect, or an additive according to either the second or third aspect.

In a sixth aspect, the present invention provides the use of an additive composition according to the fourth aspect, or an additive according to either the second or third aspect, in a lubricating oil composition to improve one or more of fuel economy and fuel economy retention of an engine, and oxidation resistance of the lubricating oil composition.

In a seventh aspect, the present invention provides a process for making a lubricating oil composition comprising blending a major amount of an oil of lubricating viscosity and a minor amount of an additive composition according to the fourth aspect, or an additive according to either the second or third aspect.

In an eighth aspect, the present invention provides a method of lubricating an internal combustion engine comprising supplying to the engine a lubricating oil composition according to the fifth aspect or made by the process according to the seventh aspect.

In a ninth aspect, the present invention provides a method for improving one or more of fuel economy and fuel economy retention of an internal combustion engine comprising treating moving surfaces thereof with a lubricating oil composition according to the fifth aspect or made by the process according to the seventh aspect.

In a tenth aspect, the present invention provides a method of reducing the amount of labile sulfur in a molybdenum-sulfur additive, said method comprises the steps of reacting an additive comprising one or more molybdenum-sulfur compounds with a compound (C) that is capable of reacting with the labile sulfur.

The features of the invention will now be discussed in more detail.

Process

It has been found that a reaction of a certain compound (C), which is capable of reacting with labile sulfur, with a molybdenum-sulfur additive is effective in making said additive more benign to copper corrosion and/or seal degradation. Preferably, the compound (C) is capable of reacting with elemental sulfur, that is sulfur which is not reacted or associated with any other species. Preferably, the products of the reaction are removed from the molybdenum-sulfur additive. Further, the resulting improved additive still has an acceptable appearance (e.g. not too dark in colour) and provides satisfactory performance properties in a lubricating oil composition.

The reaction may be carried out on a molybdenum-sulfur additive according to the tenth aspect, or, preferably, during the process for making a molybdenum-sulfur additive according to the first aspect. An advantage of carrying out the reaction during the process is that the cycle time for making the improved additive is shortened compared with the reaction according to the tenth aspect.

In the event that the reaction is carried out during the process, the compound (C) is added to a reaction mixture containing a reactant molybdenum compound (A) and a source of a ligand (B) after the reaction between (A) and (B) has begun. Preferably, compound (C) is added to and reacted with the mixture of (A) and (B) after a substantial, preferably complete, reaction of (A) and (B).

Therefore, in a process according to the first aspect, the initial step is (I) reacting, in a polar medium, a reactant molybdenum compound (A) and a source of a ligand (B) to make a molybdenum-sulfur compound.

Examples of a polar medium include tetrahydrofuran (THF), dimethylformamide (DMF), methanol, water, and any mixture thereof. A preferred polar medium for step (I) is methanol.

Examples of reactant molybdenum compound (A) are the reaction products of molybdenum trioxide or an alkaline metal or ammonium salt of molybdic acid with one or more of a sulfide, such as alkali sulfide (e.g. sodium sulfide), ammonium sulfide and alkali hydrosulfide (e.g. sodium hydrosulfide). Such reaction products may also be made in situ as part of the process according to the first aspect.

In the event that the molybdenum-sulfur additive is a trinuclear molybdenum-sulfur additive, the reactant molybdenum compound (A) is a compound containing an anion that possesses a trinuclear molybdenum core comprising at least one sulfur atom and may contain one or more other atoms selected from oxygen and selenium. Preferably, the reactant molybdenum compound (A) contains a core that is fully sulfurised, e.g. the reactant molybdenum compound (A) contains a $[Mo_3S_{13}]^{2-}$ anion, which may be present as an ammonium salt thereof; such an anion may be prepared by the process described in U.S. Pat. Nos. 3,876,755 and 4,243,554.

Examples of a ligand (B) include a dithiophosphate, a dithiocarbamate, a xanthate, a carboxylate, a thioxanthate, a phosphate and hydrocarbyl, preferably alkyl, derivatives thereof.

Sources of ligand (B) include salts of ligand (B), for example, potassium dithiophosphate and potassium dithiocarbamate; and organic disulfides, such as thiuram disulfide or hydrocarbyl, preferably alkyl, derivatives thereof, in which event the ligand (B) is a dithiocarbamate. Preferably, the ligand (B) is formed in situ during the process for making the additive, which allows for a reduction in number of processing steps for making the additive.

The molar ratio of the reactant molybdenum compound (A) to the ligand (B) is preferably from 1:1 to 1:4.

An especially preferred process for making a molybdenum-sulfur dithiocarbamate additive is a process where the dithiocarbamate ligand is made in situ; the in situ prepared dithiocarbamate ligand (B) then reacts with the reactant molybdenum compound (A).

The dithiocarbamate may be prepared in situ, for example by providing carbon disulfide and a hydrocarbyl-substituted amine such as a secondary alkylamine under conditions to react to produce the dithiocarbamate ligand (B), which, in turn, reacts with reactant molybdenum compound (A), such as $[NH_4]_2[Mo_3S_{13}]$. Also, a base, such as an alkali metal hydroxide, e.g. NaOH, may be provided for the reaction of the reactant molybdenum compound (A) and ligand (B). The molar ratio of reactant molybdenum compound (A) to carbon disulfide to amine is preferably 1:4:4 to 1:10:10, for example, including 1:10:4 and 1:4:10.

After the reaction of step (I) has begun or has been completed, step (II), the reaction with a compound (C), occurs to yield the molybdenum-sulfur additives of the present invention.

In an embodiment, a compound (C) may be added to and reacted with a mixture of (A) and (B) after the reaction of (A) and (B) has begun. Preferably, the compound (C) can be reacted with a mixture of (A) and (B) after 20, more preferably after 40, such as after 60, especially after 80, advantageously after 90, %, of the reaction in step (I) is completed.

In another embodiment, the compound (C) is reacted with the product of step (I).

The reaction conditions (for example, choice of media, temperatures and times) for the reaction of compound (C) in step (II) are typically the same whether the compound (C) is reacted in step (I) or with the product of step (I).

The reaction in step (II) is preferably carried out in a polar medium, such as tetrahydrofuran (THF), dimethylformamide (DMF), methanol, water and any mixture thereof.

Preferably, the reaction in step (II) is carried out at elevated temperatures, preferably the reaction temperature is at most 160, more preferably at most 140, especially at most 130, advantageously at most 120, such as in the range of from 40 to 100, ° C.

The reaction of step (II) according to the first aspect is carried out over a period, typically for about at least 1 hour, to ensure that the compound (C) fully reacts with the labile sulfur.

The products of the reaction of compound (C) with labile sulfur may be left in the molybdenum-sulfur additive or removed, e.g. separated, from the additive. Preferably, the products are removed.

Preferably, the products of the reaction of labile sulfur are removed from the reaction mixture without affecting the molybdenum-sulfur compound's integrity and performance effectiveness. Methods of removal include phase separation of the reaction mixture and distillation; phase separation is preferred.

A compound (C) suitable for use in the present invention is a compound that is capable of reacting with labile sulfur, such as elemental sulfur or sulfur in a polysulfide chain, but not reacting with any sulfur bonded to a molybdenum atom. Examples of such compounds (C) are:

(a) compounds that contain unsaturation, such as unsaturated carboxylic acids, e.g. oleic acid, unsaturated amines, e.g. oleylamine, olefins, preferably alpha-olefins, e.g. 1-decene; and acetylenic compounds;

(b) ammonium sulfide derivatives, such as alkyl ammonium sulfide and ammonium sulfide, $(NH_4)_2S_x$, where x is at least 1, such as less than 2;

(c) bases, e.g. sodium hydroxide; and (d) aldehydes, e.g. octanal;

The amount of compound (C) used in step (II) is that sufficient to react with all the labile sulfur; preferably it is used in an excess of that required so that all labile sulfur is reacted. A skilled person in the art would be able to determine the optimum amount needed.

It is preferred to use ammonium sulfide, especially as an aqueous solution, as compound (C) to react with labile sulfur. The ammonium sulfide may contain more than one, preferably less than two, mole(s) of sulfur, per two moles of nitrogen.

In an especially preferred embodiment, compound (C) is ammonium monosulfide, i.e. one mole of sulfur for every two moles of nitrogen, and is used in the reaction of step (II) as an aqueous solution. A skilled person would understand that commercial grades of ammonium monosulfide may comprise ammonium sulfide having, on average, more than one mole of sulfur per two moles of nitrogen; such grades are effective in the present invention provided they are capable of reacting with the labile sulfur.

In the event that an aqueous solution of ammonium sulfide is used as compound (C), it is preferred to use methanol and water as the polar medium and the desired molybdenum-sulfur additive is preferably phase separated. It has been found that better extraction of the reaction products with ammonium sulfide and better phase separation is obtained if the ratio, by mass, of methanol to water is preferably 1:10 to 10:1, more preferably 5:1 to 1:1.

The temperature of the reaction mixture in step (II) is preferably about 40 to 60, such as 45 to 55, ° C. when an aqueous solution of ammonium sulfide is used in a polar medium of water and methanol.

It has been found that, when an aqueous solution of ammonium sulfide is used in the process for making an additive according to the first aspect, especially in step (I), the yield of the additive is improved and there is less sediment and waste in the process.

The reaction of compound (C), preferably an aqueous solution of ammonium sulfide, has been found to be particularly effective on a trinuclear molybdenum-sulfur additive; examples of trinuclear molybdenum-sulfur additives are described in WO98/26030, WO99/31113, WO99/66013, EP-A-1 138 752 and EP-A-1 138 686. It is preferred that the reaction is carried out during the process for making the trinuclear molybdenum-sulfur additives, preferably trinuclear molybdenum-sulfur dithiocarbamates. An especially preferred process for making a trinuclear molybdenum-sulfur dithiocarbamate additive is when the dithiocarbamate ligand is made in situ in the process (see for example, EP-A-1 138 686), and then the resulting reaction mixture is finally reacted with the compound (C), for example, an aqueous solution of ammonium sulfide.

In a preferred embodiment of appropriate aspects of the invention, the additive comprises a diluent fluid, which aids in the handling of the additive. In the event that a diluent fluid is present in the additive, the diluent fluid may be introduced into the reaction mixture at any time during the process; it is preferred to introduce the diluent fluid after step (II).

The use of ammonium sulfide in the present process ensures that metal residues are not formed and the products from the reaction with ammonium sulfide can be easily separated from the desired molybdenum-sulfur additive. Further, the ammonium sulfide has been found to be an effective compound for reacting with labile sulfur and drive the reaction of the reactant molybdenum compound (A) and source of ligand (B) to completion. Accordingly, use of ammonium sulfide, as compound (C), in a process for making an additive comprising one or more molybdenum-sulfur, preferably, trinuclear molybdenum-sulfur, compounds results in improved yield, and reduced sediment and waste.

The conditions and preferred embodiments described above for step (II) of the first aspect are also applicable to the process according to the tenth aspect, with the difference being that, in the process according to the tenth aspect, the compound (C) is reacted with a molybdenum-sulfur additive.

Additive

The additive or molybdenum-sulfur additive, of the appropriate aspects of the invention, preferably consists essentially of, especially consists of, one or more oil-soluble or oil-dispersible molybdenum-sulfur compounds.

In an embodiment of appropriate aspects of the invention, the additive has a colour reading less than 5.0, preferably less than 4.5, more preferably less than 4.0, especially less than 3.5, advantageously less than 3.0, as measured according to ASTM D1500 on a sample containing white oil and the additive in an amount of 110 ppm by mass of elemental molybdenum, based on the mass of the sample. The additive advantageously has a colour reading of 1.5 or more, preferably 2.0 or more. The amount of elemental molybdenum is measured by ASTM D5185.

In an embodiment of appropriate aspects of the invention, independently of the other embodiments, the additive has a chlorine content of less that 800, preferably less than 600, more preferably less than 500, especially less than 400, advantageously less than 300, ppm, based on the mass of the additive. In a preferred embodiment, the chlorine content is zero.

In an embodiment of appropriate aspects of the invention, independently of the other embodiments, the sulfur to molybdenum ratio of the additive is in the range of 1.50 to 2.20 or 2.15, preferably 1.55 to 2.0, more preferably 1.60 to 1.90, especially 1.60 to 1.85. The molybdenum and sulfur contents of the additive are measured by ASTM D5185.

The molybdenum-sulfur compounds useful in the present invention may be mononuclear or polynuclear. In the event that the compound is polynuclear, the compound contains a molybdenum core consisting of non-metallic atoms, such as sulfur, oxygen and selenium.

To enable the molybdenum-sulfur compound to be oil-soluble or oil-dispersible, one or more ligands are bonded to a molybdenum atom in the compound. The bonding of the ligands includes bonding by electrostatic interaction as in the case of a counter-ion and forms of bonding intermediate between covalent and electrostatic bonding. Ligands within the same compound may be differently bonded. For example, a ligand may be covalently bonded and another ligand may be electrostatically bonded.

Preferably, the or each ligand is monoanionic and examples of such ligands are dithiophosphates, dithiocarbamates, xanthates, carboxylates, thioxanthates, phosphates and hydrocarbyl, preferably alkyl, derivatives thereof. Preferably, the ratio of the number of molybdenum atoms, for example, in the core in the event that the molybdenum-sulfur compound is a polynuclear compound, to the number of monoanionic ligands, which are capable of rendering the compound oil-soluble or oil-dispersible, is greater than 1 to 1, such as at least 3 to 2.

The molybdenum-sulfur compound's oil solubility or dispersibility may be influenced by the total number of carbon atoms present among all of the compound's ligands. The total number of carbon atoms present among all of the hydrocarbyl groups of the compound's ligands typically will be at least 21, e.g. 21 to 800, such as at least 25, at least 30 or at least 35. For example, the number of carbon atoms in each alkyl group will generally range between 1 to 100, preferably 1 to 40, and more preferably between 3 and 20.

In a preferred embodiment of appropriate aspects of the invention, the additive comprises one or more oil-soluble or oil-dispersible trinuclear molybdenum-sulfur compounds.

Independently of the nuclearity of the molybdenum-sulfur compound, the molybdenum in the compound preferably has an oxidation state of +5 or less, such as +4.

In a preferred embodiment of appropriate aspects of the invention, the additive comprises one or more molybdenum-sulfur compounds having a core of the structures depicted in (I) or (II):

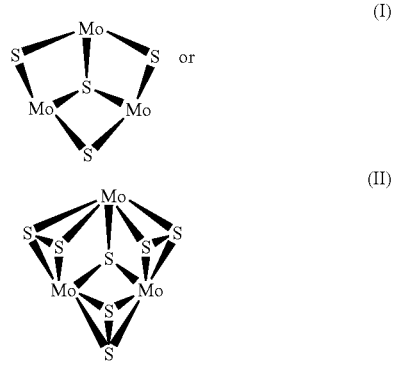

Each core has a net electrical charge of +4.

Preferably, the trinuclear molybdenum-sulfur compounds are represented by the formula $Mo_3S_kE_xL_nA_pQ_z$, wherein:

k is an integer of at least 1;

E represents a non-metallic atom selected from oxygen and selenium;

x can be 0 or an integer, and preferably k+x is at least 4, more preferably in the range of 4 to 10, such as 4 to 7, most preferably 4 or 7;

L represents a ligand that confers oil-solubility or oil-dispersibility on the molybdenum-sulfur compound, preferably L is a monoanionic ligand;

n is an integer in the range of 1 to 4;

A represents an anion other than L, if L is an anionic ligand;

p can be 0 or an integer;

Q represents a neutral electron-donating compound; and z is in the range of 0 to 5 and includes non-stoichiometric values.

Those skilled in the art will realise that formation of the trinuclear molybdenum-sulfur compound will require selection of appropriate ligands (L) and other anions (A), depending on, for example, the number of sulfur and E atoms present in the core, i.e. the total anionic charge contributed by sulfur atom(s), E atom(s), if present, L and A, if present, must be −12. The trinuclear molybdenum-sulfur compound may also have a cation other than molybdenum, for example, (alkyl)ammonium, amine or sodium, if the anionic charge exceeds −12.

Examples of Q include water, alcohol, amine, ether and phosphine. It is believed that the electron-donating compound, Q, is merely present to fill any vacant coordination sites on the trinuclear molybdenum-sulfur compound.

Examples of A can be of any valence, for example, monovalent and divalent and include disulfide, hydroxide, alkoxide, amide and thiocyanate or derivative thereof; preferably A represents a disulfide ion.

Preferably, L is monoanionic ligand, such as dithiophosphates, dithiocarbamates, xanthates, carboxylates, thioxanthates, phosphates and hydrocarbyl, preferably alkyl, derivatives thereof. When n is 2 or more, the ligands can be the same or different.

In an embodiment, independently of the other embodiments, k is 4 or 7, n is either 1 or 2, L is a monoanionic ligand, p is an integer to confer electrical neutrality on the compound based on the anionic charge on A and each of x and z is 0.

In a further embodiment, independently of the other embodiments, k is 4 or 7, L is a monoanionic ligand, n is 4 and each of p, x and z is 0.

The molybdenum-sulfur cores, for example, the structures depicted in (I) and (II) above, may be interconnected by means of one or more ligands that are multidentate, i.e. a ligand having more than one functional group capable of binding to a molybdenum atom, to form oligomers. Molybdenum-sulfur additives comprising such oligomers are considered to fall within the scope of this invention.

A diluent fluid may be used in the additive to ensure satisfactory handling of the additive, for example, so that it has a acceptable viscosity. In the event that a diluent fluid is used, the amount of diluent fluid is minimised to the extent possible. Preferably, the amount of the diluent fluid is at least 10, such as at least 30, especially at least 45, mass %, based on the mass of the additive. The amount of diluent is advantageously at most 55 mass %.

Examples of diluent fluid include suitable oleaginous, typically hydrocarbon, solvents, such as oils of lubricating viscosity selected from vegetable, animal, mineral and synthetic oils. In an embodiment, the diluent fluid is free of sulfur.

The additive may contain as much molybdenum-sulfur compound as possible, but for ease of handling the additive preferably comprises one or more molybdenum compounds in an amount of at least 4.50, more preferably at least 4.75, such as at least 5.00, especially at least 5.25, advantageously at least 5.50, for example, at least 6.00, mass % of elemental molybdenum, based on mass of the additive. The amount of elemental molybdenum in the additive is at most 7.00, such as at most 6.50, mass %, based on the mass of the additive.

Preferably, the additive of the third aspect is obtainable, more preferably obtained, by the process of the first aspect.

Additive Composition

The additive according to the second or third aspect may be present in an additive composition with one or more other co-additives.

In the preparation of lubricating oil compositions, it is common practice to introduce additives therefor in the form of additive composition(s) containing the additives in a suitable oleaginous, typically hydrocarbon, diluent fluid, e.g. mineral lubricating oil, or other suitable solvent. Oils of lubricating viscosity as well as aliphatic, naphthenic, and aromatic hydrocarbons are examples of suitable diluent fluids for additive compositions.

An additive composition constitutes a convenient means of handling two or more additives before their use, as well as facilitating solution or dispersion of the additives in lubricating oil compositions. When preparing a lubricating oil composition that contains more than one type of additive (sometimes referred to as "additive components"), each additive may be incorporated separately. In many instances, however, it is convenient to incorporate the additives as an additive composition (a so-called additive "package" (also referred to as an "adpack")) comprising two or more additives.

Examples of co-additives include dispersants, detergents, rust inhibitors, anti-wear agents, anti-oxidants, corrosion inhibitors, friction modifiers, pour point depressants, anti-foaming agents, viscosity modifiers and surfactants.

An additive composition may contain 1 to 90, such as 10 to 80, preferably 20 to 80, more preferably 20 to 70, mass % based on active ingredient, of the additives, the remainder being diluent fluid.

The amount of elemental molybdenum, derived from the additive according to either the second or third aspect, present in the additive composition is preferably in the range of 0.025 to 4 mass %, based on the mass of the additive composition.

Lubricating Oil Composition

The lubricating oil composition according to the fifth aspect is preferably a crankcase lubricating oil composition for spark- or compression-ignited engines.

The amount of elemental molybdenum derived from the additive according to either the second or third aspect in a lubricating oil composition is preferably in the range of 1 to 1000, more preferably from 20 to 500, such as 50 to 300, ppm, based on the mass of the oil composition.

The lubricating oil composition can also find application in industrial oils, for example, those used in turbines, hydraulic systems and circulation systems. The amount of trinuclear molybdenum-sulfur additives in such oils tends to be less than that found in crankcase lubricating oil compositions, typically less than 20, such as 1 to 10, for example, 2 to 8, ppm, based on elemental molybdenum.

The additive of the present invention may also find application in grease compositions.

In an embodiment of the fifth aspect, the lubricating oil composition gives less than 400, such as less than 300, preferably less than 250, especially less than 150, ppm of copper corrosion according to ASTM D6594.

Lubricating oil compositions may be prepared by adding to an oil of lubricating viscosity a mixture of an additive according to the second or third aspect and, if necessary, one or more co-additives such as described herein. The preparation may be accomplished by adding the additive directly to the oil or by adding it in the form of an additive composition according to the fourth aspect. Additives may be added to the oil by any method known to those skilled in the art, either prior to, contemporaneously with, or subsequent to addition of other additives.

The oil of lubricating viscosity can be a synthetic or mineral oil of lubricating viscosity selected from the group consisting of Group I, II, III, IV and V basestocks and any mixture thereof. American Petroleum Institute (API) 1509 "Engine Oil Licensing and Certification System" Fourteenth Edition, December 1996 defines Group I, II, III, IV and V basestocks.

Basestocks may be made using a variety of different processes including but not limited to distillation, solvent refining, hydrogen processing, oligomerization, esterification, and re-refining.

In an embodiment, lubricating oil compositions of the present invention do not comprise corrosion inhibitors.

It should be appreciated that interaction may take place between any two or more of the additives after they have been incorporated into the additive composition or lubricating oil composition. The interaction may take place in either the process of mixing or any subsequent condition to which the composition is exposed, including the use of the composition in its working environment. Interactions may also take place when further auxiliary additives are added to the compositions of the invention or with components of oil. Such interaction may include interaction that alters the chemical constitution of the additives. Thus for example the compositions of the invention include compositions in which interaction, for example, between any of the additives, has occurred, as well as compositions in which no interaction has occurred, for example, between the components mixed in the oil.

Further Technical Effects of the Invention

The molybdenum-sulfur additive of invention is effective in oxidation control of lubricating oil compositions and improving the fuel economy properties of an engine because of its demonstrated oxidation and friction reducing properties.

Further, the trinuclear molybdenum-sulfur additive of the invention has been found to demonstrate comparable performance properties to the additives described in WO98/26030, WO99/31113, WO99/66013, EP-A-1 138 686 and EP-A-1 138 752, particularly provide excellent oxidation resistance to lubricating oil compositions and good fuel economy and fuel economy retention properties to an engine.

In this specification:

The term 'molybdenum-sulfur compound' means a compound having at least one molybdenum atom and at least one sulfur atom, preferably the compound has at least one sulfur atom that is bonded to one or more molybdenum atoms and also bonded to one or more non-molybdenum atoms, such as carbon, more preferably the compound has at least one sulfur atom that is bonded to one or more molybdenum atoms only, such as represented by cores $[Mo_2S_4]$, $[Mo_3S_4]$ and $[Mo_3S_7]$. Atoms selected from oxygen and selenium may replace one or more sulfur atoms in such cores. Advantageously, the core consists of molybdenum and sulfur atoms alone. Accordingly, the term 'molybdenum-sulfur additive' means an additive comprising one or more molybdenum-sulfur compounds.

The term "labile sulfur" means sulfur that is in elemental, unreacted state, as well as sulfur occurring in polysulfide species and that may be analysed by a polargraphic method which is described in "The Analytical Chemistry of Sulfur and Its Compounds", H. I. Karchmer, Wiley Interscience, New York (1970), page 82.

The term "hydrocarbyl" as used means that the group concerned is primarily composed of hydrogen and carbon atoms and is bonded to the remainder of the molecule via a carbon atom, but does not exclude the presence of other atoms or groups in a proportion insufficient to detract from the substantially hydrocarbon characteristics of the group.

The term "comprising" or "comprises" means the presence of stated features, integers, steps or components, but does not preclude the presence or addition of one or more other features, integers, steps, components or groups thereof. In the instance the term "comprising" or comprises" is used herein, the term "consisting essentially of" and its cognate are within its scope and are a preferred embodiment of it, and consequently the term "consisting of" and its cognate are within the scope of "consisting essentially of" and are a preferred embodiment of it.

The term "oil-soluble" or "oil-dispersible" does not mean that the compounds are soluble, dissolvable, miscible or capable of being suspended in the oil in all proportions. They do mean, however, that the compounds are, for instance, soluble or stable dispersible in the oil to an extent sufficient to exert their intended effect in the environment in which the oil composition is employed. Moreover, the additional incorporation of other additives such as those described above may affect the solubility or dispersibility of the compounds.

"Major amount" means in excess of 50, such as greater than 70, preferably 75 to 97, especially 80 to 95 or 90, mass %, of the composition.

"Minor amount" means less than 50, such as less than 30, for example, 3 to 25, preferably 5 or 10 to 20, mass %, of the composition.

All percentages reported are mass % on an active ingredient basis, i.e. without regard to carrier or diluent oil, unless otherwise stated.

The term "coco" is an alkyl chain or mixture of alkyl chains of varying even numbers of carbon atoms, typically from $C_6$ to $C_{18}$.

The invention is illustrated by, but in no way limited to, the following examples.

EXAMPLES

Example 1

Treatment of a Molybdenum-sulfur Additive With Ammonium Sulfide

A trinuclear molybdenum dicocodithiocarbamate additive (1000 g), which was made by the process described in Example 1 of WO99/31113, but without the use of toluene and involved no filtration step, was added to a solution of methanol (100 g) and an aqueous solution of ammonium sulfide (250 g, 45% by mass of ammonium sulfide). The resulting mixture was heated to 40° C. and stirred for 2 hours. The mixture was then allowed to cool and settle. The mixture separated into two layers. The aqueous layer was discarded and the organic layer heated to 100° C. and a vacuum applied for 2 hours to yield the desired molybdenum-sulfur additive.

Example 2

Synthesis of a Trinuclear Molybdenum-sulfur Compound $(NH_4)_2Mo_3S_{13} \cdot 2H_2O$ (77.1 g) and dicocoamine (181.7 g) were added to a mixture of methanol (156.8 g) and base oil (114.1 g), under a nitrogen atmosphere and stirred and heated to 37° C. Carbon disulfide (20 g) was added over 2 hours at 37° C. whilst continuing to stir and then the reaction mixture was heated to 60° C. and another portion of carbon disulfide (25 g) was added over 6 hours. The mixture was then heated to reflux for 4 hours and allowed to cool to 50° C. An aqueous solution of ammonium sulfide (62.8 g, 45% by mass of ammonium sulfide) was added and stirred for 2 hours at 50° C. The mixture was then allowed to settle and the aqueous layer was discarded. Mineral oil (114.1 g) was added to the organic layer and the mixture was heated to 120° C. under nitrogen and then a vacuum applied at 120° C. for 1 hour to yield the desired molybdenum-sulfur additive.

The colour, sulfur to molybdenum ratio and chlorine content were determined for the products of Examples 1 and 2 (see Table 1). Table 1 has also those measurements for:

Additive A—an additive containing a trinuclear molybdenum dicocodithiocarbamate made by the process of Example 5 of WO98/26030, but where a potassium dicocodithiocarbamate was used instead of the potassium dilauryldithiophosphate;

Additive B—an additive containing a trinuclear molybdenum dicocodithiocarbamate made by the process described in Example 1 of WO99/31113, but without the use of toluene and involved no filtration step;

Additive C—an additive containing a trinuclear molybdenum dicocodithiocarbamate made by the process described in Example 1 of WO99/31113, but without the use of toluene and involved no filtration step, and which was then heated to about 160° C. for 4 hours; and Additive D—a commercial molybdenum additive sold by Vanderbilt Chemical Company under the brand name MOLYVAN 822.

TABLE 1

|  | colour[p] | sulfur to molybdenum ratio[q] | chlorine[r], ppm |
| --- | --- | --- | --- |
| Example 1 | 4.0 | 1.67 | 50 |
| Example 2 | 5.0 | 1.63 | 70 |
| Additive A | 4.0 | 1.85 | 1000 |
| Additive B | 4.0 | 2.33 | 80 |
| Additive C | 6.0 | 1.65 | 60 |
| Additive D | 1.0 | 1.03 | — |

[p]ASTM D1500 measured on a sample containing white oil and the additive in an amount of 110 ppm by mass of elemental molybdenum: the lower the reading the paler the sample;
[q]sulfur and molybdenum amounts were measured by ASTM D5185;
[r]measured by x-ray fluorescence;
a dash indicates no measurement was taken.

Table 1 shows that the trinuclear molybdenum-sulfur additives of the art contain chlorine (e.g. Additive A) or have a high sulfur to molybdenum ratio (e.g. Additive B) or are dark in appearance (e.g. Additive C). In contrast, the additives of invention (Examples 1 and 2) do not suffer from any of those disadvantages and exhibit satisfactory properties.

Table 2 shows the effect a molybdenum-sulfur additive has on a finished lubricating oil composition in respect of colour and copper corrosion.

TABLE 2

|  | colour[s] | HTCBT[t] - Cu, ppm |
| --- | --- | --- |
| Oil 1 | 3.0 | 147.4 |
| Oil 2 | 3.5 | 113.9 |
| Oil B | 2.5 | 426.9 |
| Oil C | 7.0 | 148.6 |

[s]ASTM D1500 measured directly on the oil;
[t]High Temperature Corrosion Bench Test (HTCBT): ASTM D6594;
the oil designations 1, 2, B and C correspond to which molybdenum-sulfur additive is used in the finished oil composition (see Table 1).

From Table 2, a molybdenum-sulfur additive having a high sulfur to molybdenum ratio (e.g. Additive B) gave poor copper corrosion (see Oil B). While a molybdenum-sulfur additive having a high colour (e.g. Additive C) gave poor colour also in the finished lubricating oil composition (see Oil C). In contrast, Oils 1 and 2, which contained the molybdenum-sulfur additives of the present invention, demonstrate satisfactory performance in respect of colour and copper corrosion. The lubricating oil compositions (Oils 1, 2, B and C) were identical except for the type of molybdenum-sulfur additive used and each molybdenum additive was blended to 200 ppm of elemental molybdenum.

Oil 2 was also found to have satisfactory oxidation control and friction-reducing performance. For comparison, the data for a non-molybdenum containing lubricating oil composition is also given (see Oil E): Oil E was identical to Oil 2 but no molybdenum additive was used.

TABLE 3

|  | Oxidation CHP[u] | Friction[x] average friction @ 140° C., μ |
|---|---|---|
| Oil 2 | 1.19 | 0.09 |
| Oil E | 0.20 | 0.15 |

[u]amount of Cumene Hydroperoxide (CHP) degraded at 125° C. for one hour, in millimoles of CHP degraded per gram of oil, is an indicator of the oxidation potential of the oil;
[x]High Frequency Reciprocating Rig operated over 30 minutes.

What is claimed is:

1. A process for making an additive comprising one or more oil-soluble or oil-dispersible molybdenum-sulfur compounds, said process comprising the steps of:
   (I) reacting in a polar medium a thiomolybdate salt (A) and a source of a ligand (B), which ligand (B) is capable of rendering the or each thiomolybdate salt oil-soluble or oil-dispersible; and
   (II) reacting a compound (C), which is capable of reacting with labile sulfur, either with (a) the reaction mixture of step (I) after the reaction of (A) and (B) has begun or (b) with the product of step (I), wherein compound C is ammonium sulfide or a derivative thereof.

2. The process of claim 1 wherein the or each thiomolybdate salt is a trinuclear molybdenum-sulfur compound.

3. The process of claim 1 wherein the thiomolybdate salt (A) contains an anion and possesses a trinuclear molybdenum core comprising at least one sulfur atom.

4. The process of claim 1 wherein the ligand (B) is produced in situ.

5. The process of claim 4 wherein the ligand (B) is capable of becoming negatively charged.

6. The process as claimed in claim 1, further comprising the steps of:
   (III) separating the reaction mixture of step (II) into aqueous and organic phases; and
   (IV) recovering molybdenum-sulfur compound from the organic phase.

7. An additive obtained by the process claimed in claim 6.

8. An additive composition comprising a diluent fluid, an additive as claimed in claim 7, and one or more co-additives.

9. A lubricating oil composition comprising a major amount of an oil of lubricating viscosity, and added thereto or admixed therewith, a minor amount of an additive as claimed in claim 7.

10. A method of improving one or more of fuel economy and fuel economy retention of an engine, and oxidation resistance of the lubricating oil composition comprising adding to a lubricating oil composition an additive as claimed in claim 7, and lubricating an engine with said lubricating oil composition.

11. A method of improving one or more of fuel economy and fuel economy retention of an engine, and oxidation resistance of the lubricating oil composition comprising adding to a lubricating oil composition an additive composition as claimed in claim 8, and lubricating an engine with said lubricating oil composition.

* * * * *